US008760665B2

(12) United States Patent
Ume et al.

(10) Patent No.: US 8,760,665 B2
(45) Date of Patent: Jun. 24, 2014

(54) HIGH SPEED AUTOFOCUS INTERFEROMETRIC INSPECTION SYSTEMS AND METHODS

(75) Inventors: Ifeanyi Charles Ume, Atlanta, GA (US); Tyler Randolph, Trenton, GA (US)

(73) Assignee: Georgia Tech Research Foundation, Atlanta, GA (US)

( * ) Notice: Subject to any disclaimer, the term of this patent is extended or adjusted under 35 U.S.C. 154(b) by 253 days.

(21) Appl. No.: 13/203,752

(22) PCT Filed: Jan. 26, 2010

(86) PCT No.: PCT/US2010/022103
§ 371 (c)(1),
(2), (4) Date: Oct. 17, 2011

(87) PCT Pub. No.: WO2010/098921
PCT Pub. Date: Sep. 2, 2010

(65) Prior Publication Data
US 2012/0033198 A1 Feb. 9, 2012

Related U.S. Application Data

(60) Provisional application No. 61/156,060, filed on Feb. 27, 2009.

(51) Int. Cl.
*G01B 11/02* (2006.01)
(52) U.S. Cl.
USPC .......................................................... 356/502
(58) Field of Classification Search
USPC .............................. 356/432, 502; 73/588, 655
See application file for complete search history.

(56) References Cited

U.S. PATENT DOCUMENTS

| 6,075,603 | A * | 6/2000 | O'Meara et al. ............... 356/496 |
| 6,747,268 | B1 * | 6/2004 | Ume ........................ 250/227.11 |
| 7,492,449 | B2 * | 2/2009 | Ume et al. .................. 356/237.1 |
| 8,269,979 | B2 * | 9/2012 | Klein et al. .................... 356/502 |

OTHER PUBLICATIONS

Park, Hee Su et al. "Detection of laser-generated ultrasound based on phase demodulation technique using a fibre Fabry-Perot interferometer". Measurement Science and Technology, 2005, pp. 1261-1266.*

* cited by examiner

*Primary Examiner* — Michael A Lyons
(74) *Attorney, Agent, or Firm* — Troutman Sanders LLP; Ryan A. Schneider

(57) ABSTRACT

High speed autofocus interferometric inspection systems and methods are discussed in this Application. In accordance with some embodiments, an inspection system can generally include a laser module, an interferometer module, and a system controller. The laser can produce laser pulses to excite a device such as a silicon wafer, chip capacitor or chip packaged/silicon die containing a plurality of solder bumps into vibration. The interferometer module can be disposed to receive reflected laser energy from the device to sense vibration displacements created in the device with the laser pulses. The system controller to receive vibration data from the interferometer, the system controller configured to output a control signal for adjusting a relative distance and position between the laser module and the device. Other aspects, features, and embodiments are also claimed and discussed.

44 Claims, 6 Drawing Sheets

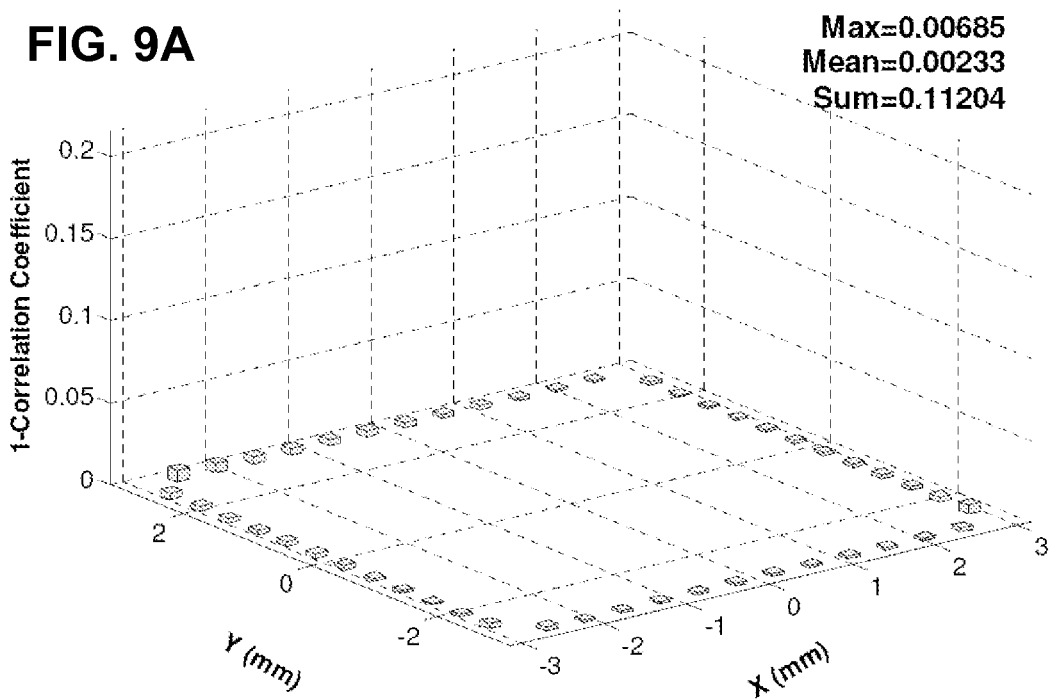
Fig. 9a: Typical Correlation Coefficient Plot for Reference Chip vs. Good Chip
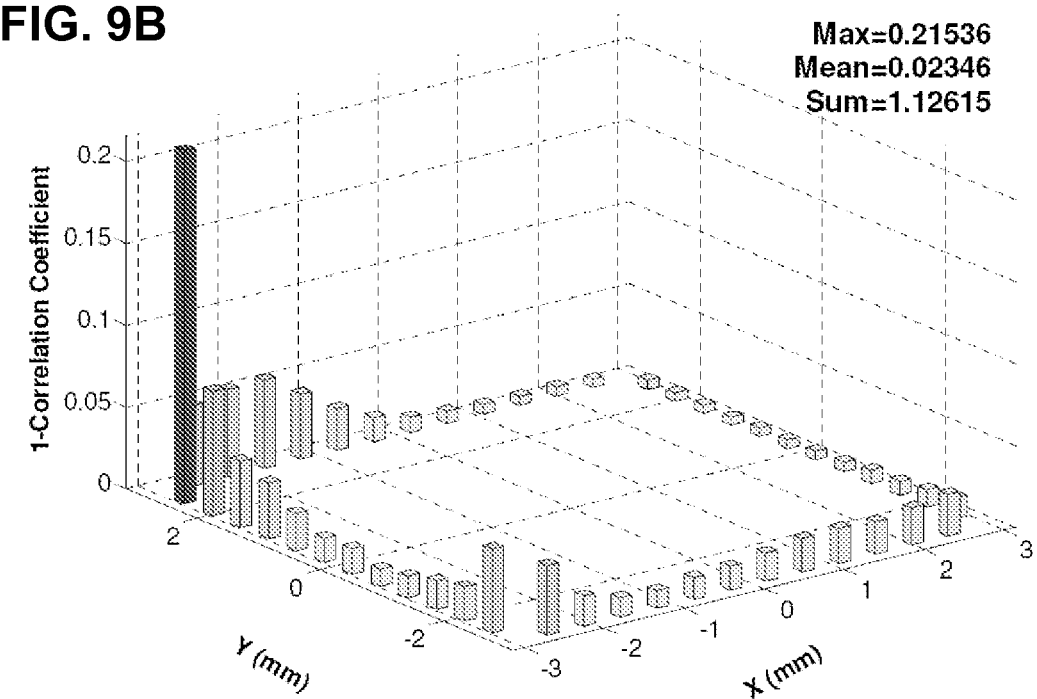
Fig. 9b: Typical Correlation Coefficient Plot for Reference Chip vs. Defective Chip

HIGH SPEED AUTOFOCUS INTERFEROMETRIC INSPECTION SYSTEMS AND METHODS

CROSS REFERENCE TO RELATED APPLICATIONS

This patent application claims the benefit of and priority to U.S. Provisional Patent Application No. 61/156,060, filed on 27 Feb. 2009, and entitled "High-Speed Autofocus Interferometric Inspection System," which is hereby incorporated by reference as if fully set forth below. Embodiments of the present invention may also utilize technology disclosed in U.S. Pat. No. 6,747,268, which is also hereby incorporated herein by reference as if fully set forth below.

FEDERALLY SPONSORED RESEARCH STATEMENT

Embodiments of the invention described herein were made with Government support under National Science Foundation Grant Number CMMI-0653730. The Government has certain rights to inventions claimed and described in this patent application.

TECHNICAL FIELD

Embodiments of the present invention relate generally to printed circuit board assembly (PCBA) manufacture and more specifically to systems and methods to test integrity of solder joints or bumps used to attach integrated circuit chips, chip packages, and chip capacitors to PCBs and substrates.

BACKGROUND

Integrated circuit (IC) packages provide power and signal interconnects while also providing protection and heat dissipation to IC electronics. For most applications, conventional ICs use lead-frame package designs like a small-outline integrated circuit for power and signal distribution to the printed circuit board (PCB) or substrate. These packages have made surface-mount devices popular. They have, however, difficulty being integrated into performance applications where a high density of interconnects is needed and where size and weight are important factors.

Several alternative packages have emerged to address these issues and limitations to the lead-frame package design. Some examples are flip chip packages (FCPs), chip scale packages (CSPs), stacked dies (STDs), stacked packages (STPs), ball grid array (BGA) packages, and system in packages (SiPs). These alternative packages use solder bumps on the bottom side of the chip to connect to PCBs or substrates. Although the use of solder bumps to connect the PCB or substrate has many advantages over lead-frame package in size and interconnect density, concerns over thermo-mechanical reliability and defective solder bump detection exist because solder bumps are hidden from view. For example, residual stresses on solder bumps after a reflow process can produce significant strain on the solder bumps, leading to bump cracking and delamination.

Some have suggested that as much as 40% of IC package defects are due to soldering problems. Because of this, it is important to monitor solder bump quality after assembly to a PCB or substrate. The ability to detect faults in solder bumps is not only important for quality, but when faults are detected early, corrective action can be taken, reducing costly rework and producing a high quality product at a low cost.

In addition, in conventional fabrication processes, faulty solder joint detection methods are typically done by humans. While generally capable of detecting defective solder joints, the process is generally slow. And when considering that PCBs or substrates have multiple chips that need testing for defects, the testing of different chips can lead to additional inefficiencies.

What is needed, therefore, are improved systems and methods enabling detection of defective solder bumps or joints. It is to the provision of such testing devices, systems, and methods that the various embodiments of the present invention are directed.

BRIEF SUMMARY OF EXEMPLARY EMBODIMENTS

Embodiments of the present invention are aimed at addressing the above-mentioned problems as well as others existing in the art. As discussed herein, embodiments of the present invention include high-speed autofocus interferometric systems and methods. Embodiments also include noncontact, nondestructive inspection techniques for investigating solder bump and joint integrity. Embodiments of the invention can advantageously detect misaligned, bridged, shorted, missing, cracked, voided, delaminated, non-wetted, partially connected, open, excessive, head-in pillow, non-wetted, and starved solder bumps. Embodiments of the present invention also provide systems and methods capable of automating the process of detecting defective solder bumps or joints for any number of chip packages on a PCB.

Generally described according to some embodiments, a testing system/method can provide a pulsed infrared laser to be directed onto a surface of an IC chip package. The laser causes rapid heating and cooling of the surface and creates elastic stress waves propagating through the IC chip package. The broadband, laser-generated ultrasound excites the natural modes of the vibration in the chip. A laser vibrometer can be positioned to sense and measure out-of-plane displacement of the chip's surface at one or more locations. Because the solder bumps are acting as mechanical constraints to vibrations produced by the laser, defects in the solder bumps or chip itself can alter the chip's vibrational response. Implementing signal processing techniques, the chip's vibrational response can be compared to a vibrational response of a well-attached chip. Based on this comparison, different types of defects can be identified.

Embodiments of the present invention can posses several advantageous features. As an example, with the excitation and measurement of the chip being done by lasers, it truly is a full-noncontact method. The excitation laser power is kept low enough not to damage the surface of the chip, making it nondestructive. Embodiments of the present invention can also provide a direct indication of solder bump integrity by inspecting a structural vibrational response of the solder bump instead of merely looking at a picture of it (e.g., an X-ray image). In addition, embodiments of the present invention enable defect detection based on a few measurements at set locations. Alternatively, measurements can be made by scanning the laser interferometer across the surface of the IC chip package. Either of these techniques enables a fast inspection relative to other techniques, making it suitable for online applications.

Measuring vibrations with lasers has many advantages over other sensor types. One significant advantage is that the measurement method does not disturb the surface vibration while providing a flat broadband frequency response and fine sub-nanometer resolution with a single sensor. By limiting the bandwidth of the vibrometer to a range of about 25 kHz to about 2 MHz, the noise level can be reduced to approximately 0.07 nm. Signal processing is utilized to eliminate low frequencies, eliminating the need for extensive environmental vibrational isolation for the vibrometer. Vibrometers used in some embodiments include a laser heterodyne interferometer, which uses the Doppler affect to measure displacement through changes in frequency shift.

One aspect of embodiments of the present invention is to maintain a strong vibrometer signal intensity strength. It has been found that the signal strength, which is the measure of the amount of light coupled back into the vibrometer focusing head, is correlated to error in a vibration waveform, resulting in the need to adjust the vibrometer at a large percentage of the measurement locations to maintain strong signal strength. Current auto-focusing vibrometers take a relatively long time to refocus (approximately 10 sec for the Polytec OFV-505, for example) resulting in the need for a higher speed system to maintain signal intensity strength.

Now turning to additional exemplary embodiments, some embodiments are directed to non-destructive inspection systems for testing silicon dies, silicon wafers, chip capacitors, and solder bumps deposited on a device. Such systems can generally comprise a laser module, an interferometer, and a system controller. The laser module can produce a pulsed laser beam. The laser beam can be positioned to excite, silicon dies, silicon wafers, chip capacitors, or devices containing a plurality of solder bumps. The excitation can cause vibration. The interferometer module can be disposed to receive reflected laser energy to sense vibration displacements created with the laser. The system controller can receive vibration data from the interferometer. The system controller can be configured to output a control signal for adjusting a relative distance between the laser module and the device.

Other embodiments include methods to test silicon dies, silicon wafers, chip capacitors and solder bumps in a device. Methods can include directing a laser at silicon dies, silicon wafers, chip capacitors, and devices comprising a plurality of solder bumps so as to make these items vibrate. Methods can also include receiving vibration data with an interferometer and adjusting a distance between the laser and at silicon dies, silicon wafers, chip capacitors, and devices in response to received vibration data to focus the interferometer.

Still yet other embodiments include inspection systems to detect defective silicon dies, silicon wafers, chip capacitors and solder bumps. Such inspection systems can generally include a vibrometer and a system controller. The vibrometer can be disposed in a position to scan a device by sensing vibrational data from a device. The device can be a silicon die, silicon wafer, chip capacitor, or many other devices comprising a plurality of solder bumps. The system controller can be in electrical communication with the vibrometer. The system controller can also be configured to receive vibrational data. Also, the system controller can be configured to process the vibrational data to determine whether silicon dies, silicon wafers, chip capacitors, or any one of the solder bumps is defective. In some embodiments, the tested device could be a chip package or silicon die populated with solder bumps and attached to a PCB or substrate, or it could be a silicon wafer or chip capacitor.

Other aspects and features of embodiments of the present invention will become apparent to those of ordinary skill in the art, upon reviewing the following description of specific, exemplary embodiments of the present invention in conjunction with the accompanying figures. While features of the present invention may be discussed relative to certain embodiments and figures, all embodiments of the present invention can include one or more of the advantageous features discussed herein. In other words, while one or more embodiments may be discussed as having certain advantageous features, one or more of such features may also be used in accordance with the various embodiments of the invention discussed herein. In similar fashion, while exemplary embodiments may be discussed below as system or method embodiments it is to be understood that such exemplary embodiments can be implemented in various systems, and methods. Embodiments of the present invention can be implemented with hardware components, software logic, or a combination of both.

BRIEF DESCRIPTION OF FIGURES

FIG. 9 (collectively FIGS. 9A & 9B) illustrates sample correlation plot diagrams showing comparisons of good and bad chips versus reference data to show how embodiments of the present invention can assist in differentiating between good and defective devices and/or solder bumps within devices.

DETAILED DESCRIPTION OF PREFERRED & ALTERNATIVE EMBODIMENTS

Figure 1:
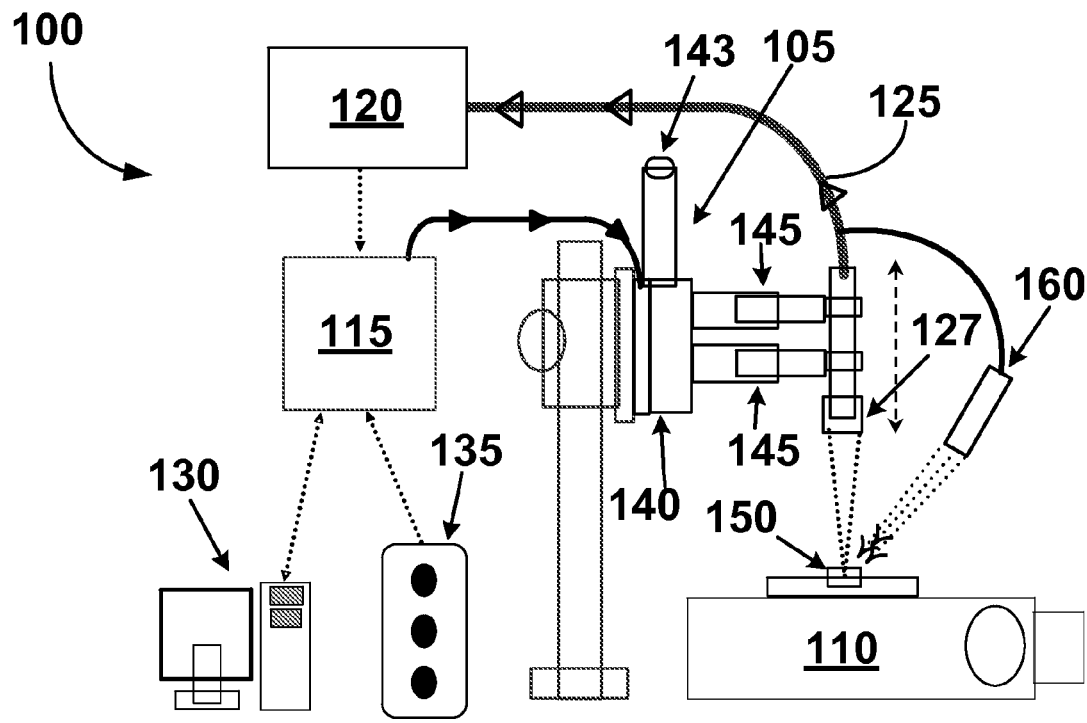
FIG. 1 depicts a vibrometer signal testing system in accordance with some embodiments of the present invention.

To facilitate an understanding of the principles and features of the various embodiments of the invention, various illustrative embodiments are explained below. As will be explained below, embodiments of the present invention provide systems and methods and systems for non-destructive inspection of solder bumps used to attach IC packages to PCBs or substrates. Advantageously, embodiments of the present invention can implement and provide fast testing methods that are accurate, repeatable, reliable, and fast. Referring now to the figures, wherein like reference numerals in some instances represent like parts throughout the views, exemplary embodiments of the present invention are described in detail.

FIG. 1 depicts a vibrometer signal auto focus system 100 in accordance with some embodiments of the present invention. Generally, the auto focus system 100 can comprises of a motorized linear stage 105, an X-Y motion stage 110, a controller module 115, a laser/vibrometer module 120 (sometimes referred to as vibrometer), an optical cable 125, an operator interface 130 (e.g., a computer), and an operator controller 135 (e.g., a remote control). It should be understood that while some embodiments of the present invention include all of the illustrated components, not all are desired for all embodiments.

As illustrated, the auto focus system 100 is a stand-alone system providing an automated signal intensity adjustment system for assisting in testing solder joints for ICs and PCBs. The laser/vibrometer module 120 is preferably adapted or configured to provide an optical signal (e.g., a laser signal) through the optic cable 125 to a vibrometer head 127. The vibrometer head 127 can direct and/or focus an optical signal to an IC/PCB module 150 disposed on the X-Y motion stage 110.

For example, the laser module 160 can provide a pulsed laser beam to be directed to an IC/PCB module's 150 solder bumps (solder balls) to enable non-destructive testing of solder bumps. Solder bumps act as mechanical constraints, and defects in the solder bumps affect the IC/PCB module's vibrational response. The vibrometer head 127, by emitting and receiving reflected laser signals, can measure the vibrational response of an IC/PCB module produced by the pulsed laser beam emitted by 160. The measured vibrational response can be compared to a known reference, and results of the comparison can provide information about the IC/PCB module's solder bumps. In some embodiments, the known reference can be vibration response data of a known good IC/PCB module. In addition, results of comparison with known data can be used to identify and category solder bump defects. Using this data, remedial actions in fabricating processes can be taken to ensure fabrication processes are yielding structurally sound IC packages.

The system 100 can also include other components for use in testing and inspecting IC packages. For example, the linear stage 105 can comprise a motorized linear actuator 140. The linear actuator 140 can have a telescoping mount 145 that gives adaptability to the where the vibrometer head 127 is located. The telescoping mount enables the vibrometer head 127 to be moved in parallel fashion with the IC/PCB module 150. The linear stage 105 can also have a stepper motor 143. The stepper motor 143 can be used to control vertical movement of the vibrometer head 127 relative to the IC/PCB module 150. The stepper motor 143 can have a resolution of 0.5 micro-meters per step in some embodiments and various other desired resolutions in other embodiments. A fine resolution value can be used to finely control the standoff distance between the vibrometer head 127 and the IC/PCB module 150. Controlling the standoff distance is how the laser/vibrometer module's 120 signal intensity strength can be adjusted. The signal intensity strength can also be adjusted by positioning the IC/PCB by movement of the X-Y stage 110.

The system 100 can also include other features. For example, the mechanical carrier carrying and/or holding the vibrometer head 127 can be configured to be substantially vibration free. This enables limited vibration of the vibrometer head 127 so that the receiving of return vibrational energy is not affected by stray mechanical vibrations. In some embodiments, the system 100 can be controlled by a user with a remote control 135 with buttons for manual input of commands or through a network connection (e.g., a serial cable) to a computer for automated control. An embodiment of system 100 can also be used to obtain the required auto focusing parameters, which will be discussed in more detail below, in an automated manner.

Figure 2:
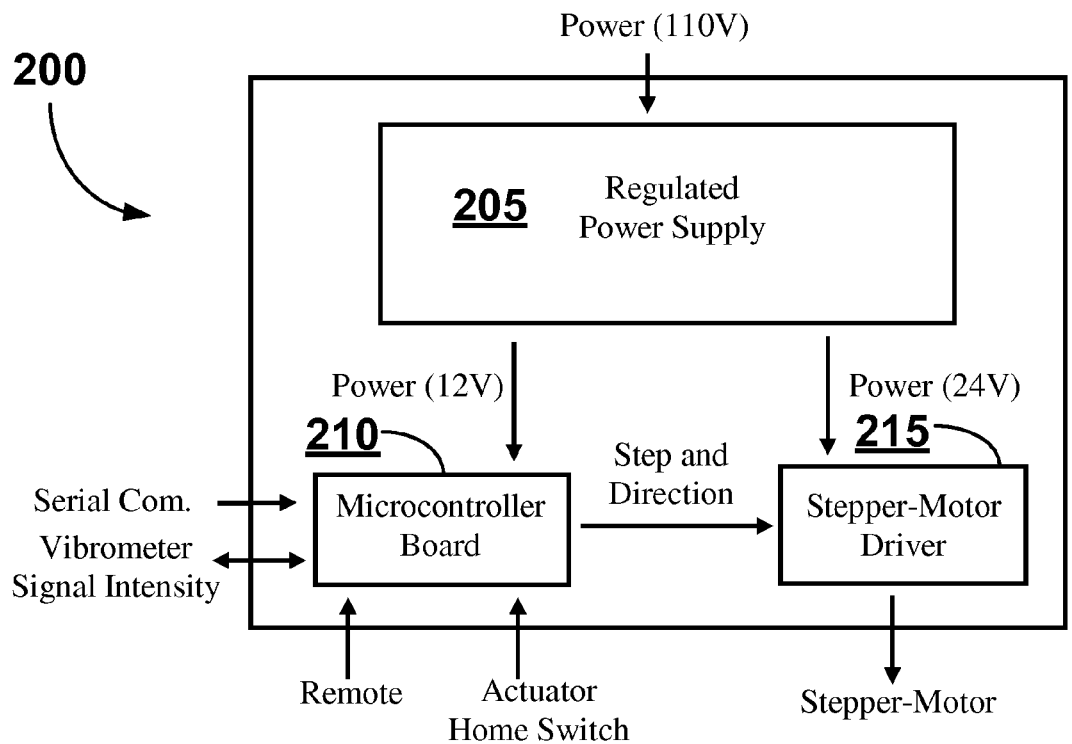
FIG. 2 graphically illustrates a functional block diagram of a controller for a high-speed auto focus interferometric testing system in accordance with some embodiments of the present invention.

FIG. 2 graphically illustrates a functional block diagram of a controller 200 for a high-speed autofocus interferometric testing system in accordance with some embodiments of the present invention. As shown, the controller can comprise a power supply 205, a processor or microcontroller 210, and a motor driver 215. The power supply 205 can receive a supply voltage and adjust as desired or needed to power the processor 210 and the motor driver 215. The processor 210 can receive data inputs, process data inputs according to pre-stored algorithms (e.g., firmware or logic), and provide data outputs. Provision of data outputs can include control signals provided to various other system components so that the controller 200 is a system controller.

In some embodiments, the controller 200 can be the controller 115 component illustrated in FIG. 1 (and for brevity, controller 200 will generally be described relative to components picture in FIG. 1). The controller 200 can be coupled to the motorized linear stage 105 and the vibrometer 120. This connectivity enables the controller 200 to receive the vibrometer's 120 signal intensity as an input signal so that the controller 200 can output a desired motorized linear stage 105 position. By doing so, the controller 200 can control the movement of the motorized linear stage 105 to move in a vertical fashion (which in turn vertically moves the vibrometer head 127) so that a desired signal intensity is obtained. To implement appropriate vibrometer head 127 movements, embodiments of the present invention can use one or more signal intensity adjustment algorithms. By using adjustment algorithms, vibrometer testing time can be minimized while maintaining test accuracy and repeatability.

Signal intensity adjustment algorithms are preferably configured to accomplish several purposes. A first purpose is to obtain test repeatability and ease of use. This can include configuring the system 100 to operate for a wide variety of inspection configurations. Different configurations, for example, can involve different thicknesses of boards, chip layouts, and the need to adjust a single time or multiple times for multiple measurements. Commands to adjust by an operator and easy control over an algorithm's parameters are also preferable to allow the system 100 to be quickly adapted to changing desires or needs. A second purpose is that signal intensity adjustment algorithms must accommodate the ability to be configured for a specific inspection configuration to optimize for a measurement system in an online inspection capacity.

Signal intensity adjustment algorithms can be utilized in various manners according to embodiments of the present invention. Those of skill in the art will appreciate that algorithms can be stored as logic in a memory for execution by a processor (such as processor 210). In addition, data storage can be various forms of memory that can be accessed a processor (such as processor 210). In some embodiments, the processor 210 can include an onboard memory (such as flash memory) for storing logic to control and implement a high speed interferometer testing systems and methods. In other embodiments, the processor 210 may access a stand-alone memory when executing a signal intensity adjustment algorithm. The inventors have devised several algorithms with currently preferred samples being discussed below and herein.

An initial signal intensity adjustment algorithm is based on an assumption that when the vibrometer head 127 is out of focus, vibrometer 120 signal intensity strength is low. The strength of the signal intensity input would then increase to a peak and then decrease back to a very low strength. This correlates to the spot size of the laser on the IC's surface 150. As the vibrometer head 127 moves out of focus, the spot size of the laser increases giving a lower light density, which reduces the amount of light that can be reflected back to the vibrometer head 127 producing a weak signal. The peak of the curve generated by this sweep would then give an optimal standoff height. A study was conducted to learn how the signal intensity strength changed during a scan as described above.

Figure 3:
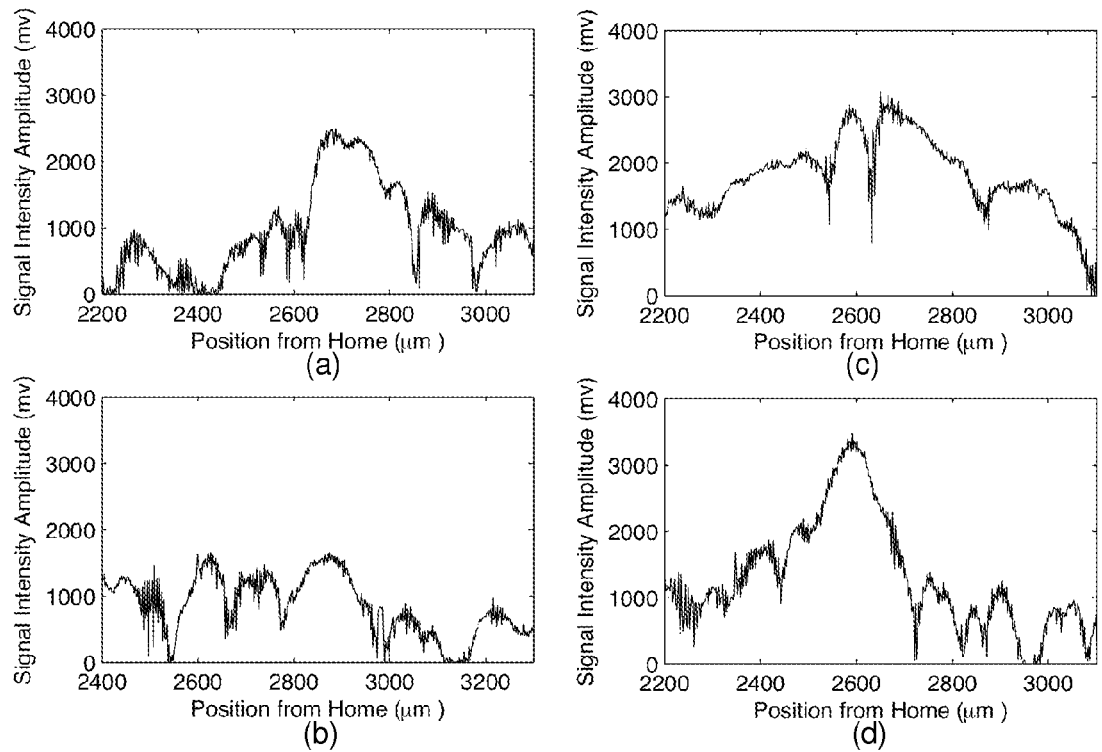
FIG. 3 shows scan profiles of four flip chip packages made by a signal intensity adjustment system according to some embodiments of the present invention.

FIG. 3 shows scan profiles for four flip chip packages made by a signal intensity adjustment system according to some embodiments of the present invention. These scan profiles illustrate how signal intensity changes with respect to standoff height with a fixed focal length. This test was performed by first moving a focusing head (e.g., the vibrometer head 127) to a home position of the linear actuator (home position meaning the linear actuator being positioned as lowest standoff height such that linear stage is not at all extended vertically up). The focusing head was then moved up in repeated increments and data taken at each increment. In the study, the focusing head was moved up 2 steps (1 µm) where the microcontroller took 10 samples of the signal intensity strength at a sampling rate of 6.25 kHz. The study repeated this move-and-sample routine until reaching a travel height of 10,000 steps (5 mm) (this height is far above the optimal focus location for most applications). These 10 samples taken at each 2 step (1 µm) increment where averaged to produce the scan profiles in FIG. 3. The signal strength scale (Y-axis) was held constant for comparison purposes while the standoff height scale (X-axis) was shifted to window the peak.

The scan profiles in FIG. 3 show a large variability in the peak amplitude and the specific curve shapes. Most notably, the presence of large local maximums near a global maximum peak made the detection of the global maximum problematic. This global maximum is what indicates the optimal focus standoff height for the vibrometer head 127. Due to this, the method chosen to find the global maximum was to scan over a region and then return to the location with the highest amplitude. This method is slower than other peak-finding algorithms, but has the highest reliability of finding the global maximum with the above mentioned difficulties.

In some embodiments of the present invention, it is currently preferred to have two phases or stages of a signal intensity adjustment algorithm: an initial adjustment phase and a readjustment phase. The initial adjustment enables an adjustment system to find the global maximum (optimal focus standoff height) with no prior knowledge about chip package geometry. The readjustment phase uses the previous global maximum as a starting point for finding a second global maximum. There are two stages to the initial adjustment phase. First, a fast, inaccurate full scan is conducted to find a general starting point; second, a slower, more precise, narrower scan for the actual optimal global maximum is performed. After completion of the two-part initial adjustment phase, the second phase can be utilized for any desired or necessary readjustments.

Figure 4:
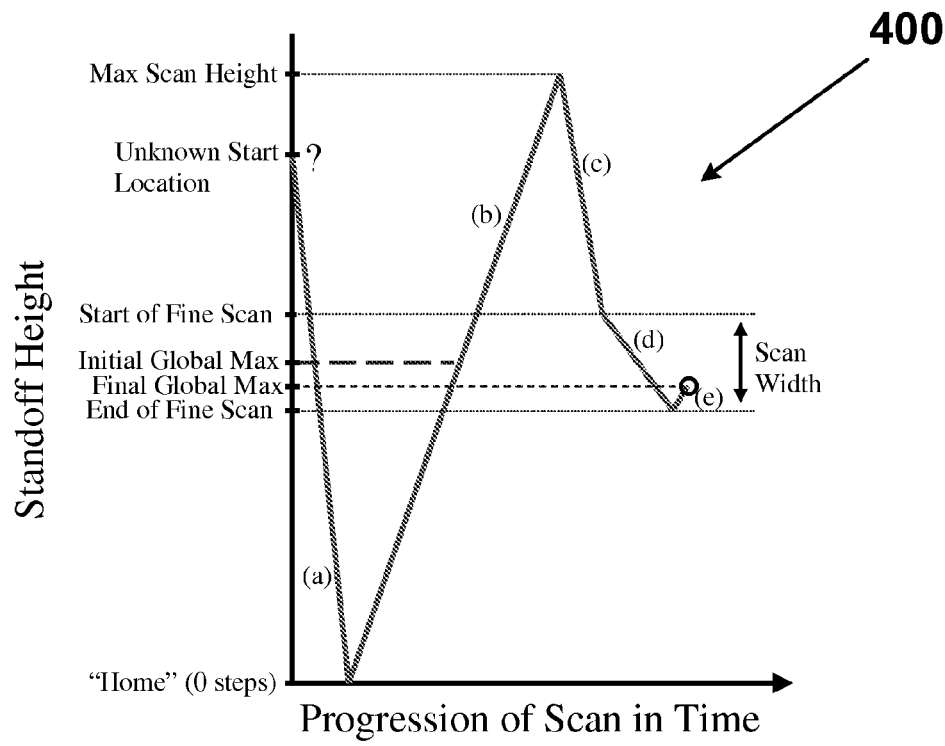
FIG. 4 illustrates a timing diagram showing a testing adjustment method in accordance with some embodiments of the present invention.

FIG. 4 illustrates a timing diagram 400 showing a testing adjustment method in accordance with some embodiments of the present invention. The timing diagram illustrates how the focusing head (e.g., the vibrometer head 127) moves as an IC/PCB scan is progressing. As illustrated, the scan can initiate with an initial adjustment routine, from an unknown linear stage starting location to a standoff height that produces a strongest signal intensity found (the global maximum of the scan). The scan continues through several movements, identified as Lines (a), (b), (c), (d), and (e), all of which are detailed below. These lines are not velocity curves and are only intended to give a general idea of the motion.

Line (a) represents the linear actuator moving from an unknown starting location to the home position at full speed. This is because the linear actuator is driven by a stepper motor with no positional feedback. When the system is started, the actuator needs to have a repeatable reference point from which dead reckoning is based.

Line (b) shows the system scanning from the home position to the max scan height. The speed with which this is done is determined by the number of steps between data points, standoff height resolution, and the number of signal intensity strength samples averaged at each data point, and this will be discussed below. The purpose of this phase of the scan is to quickly find a general starting point to look for a precise final global maximum. As the system scans up, the location (in steps) of the maximum value of the signal intensity input to the microcontroller is recorded.

Line (c) shows the focusing head moving back down to the start position of the fine scan at full speed. The start location of the fine scan is the initial global maximum plus half of the scan width. The scan width will be discussed below. This movement will center the fine scan on an initial guess of the global maximum.

Line (d) shows the focusing head scanning down to the end position of the fine scan. This scan is slower than that conducted by line (b) with a finer standoff height resolution and larger number of samples of the signal intensity strength averaged at each data point. Similar to the scan by line (b), the location of the maximum signal intensity is recorded.

Finally, line (e) shows the focusing head moving back up at full speed to the precise global maximum. Both the scan width and the parameters of the fine scan will be discussed below as part of the discussion regarding the readjustment algorithm phase.

An example of how the scan parameters discussed above can be obtained is described below. It should be noted that the results shown are specific to the IC being tested on and must be conducted for each IC/PCB type to obtain its unique optimal parameters. A test was conducted to determine the standoff height resolution and number of samples of the signal intensity strength that were averaged at each data point by iterating through 100 permutations of standoff height resolution and number of samples averaged at each data point, both going from 1-19 in 2 step increments. For each permutation, the initial adjustment routine was conducted at the given parameters; the maximum signal intensity strength that was found and its standoff height were recorded. This scan was performed 10 times for each permutation.

Figure 5:
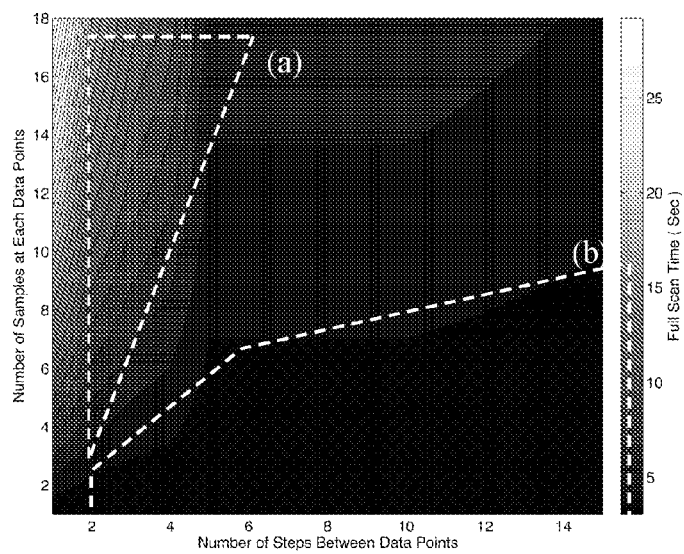
FIGS. 5-7 illustrate several contour plots of obtained during a study of an embodiment of a signal intensity adjustment system operated in accordance with some embodiments of the present invention.

FIG. 5 shows a contour plot of the time needed to conduct an initial adjustment routine (full scan) of each permutation in seconds. As seen in FIG. 5's region (a), the time to conduct a full scan at high resolution of both standoff height and number of samples averaged takes a relatively large amount of time. Region (b) shows the permutations of the full scan that have the desirable shorter scan time.

Figure 6:
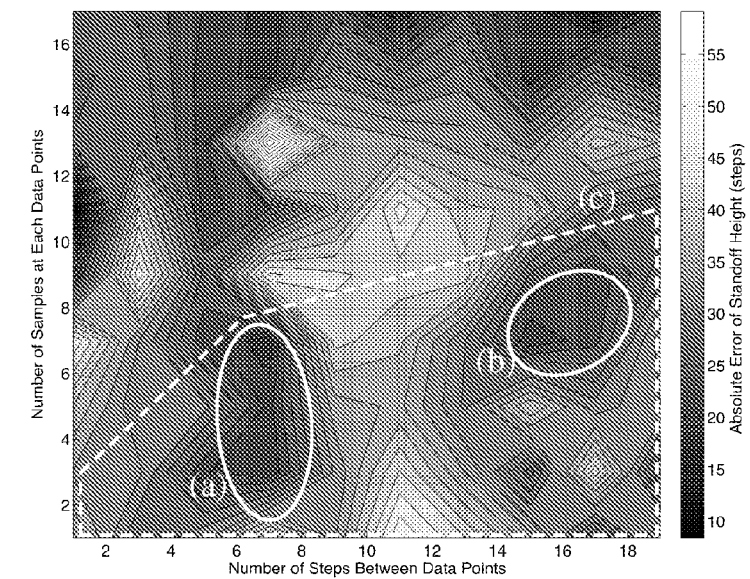

FIG. 6 shows a contour plot of the error of each permutation's optimum standoff height in steps. The error was calculated by finding the absolute difference between the permutation's global maximum and a reference global maximum. In this case, the reference global maximum was found by conducting 20 full scans at the given location with the best resolution (1 step, 0.5 µm) and 200 samples of the signal intensity strength averaged at each data point. The average of these 20 scans produced the reference global maximum. A reference global maximum was found for each different location that was scanned. As seen in the color bar, the darkest areas represent permutations with low error and are most desirable. FIGS. 6 (a) and (b) both have fairly low error and are in the faster scan time region (c) making them potential candidates. To determine which region is most desirable, the standard deviations of the permutations were investigated.

Figure 7:
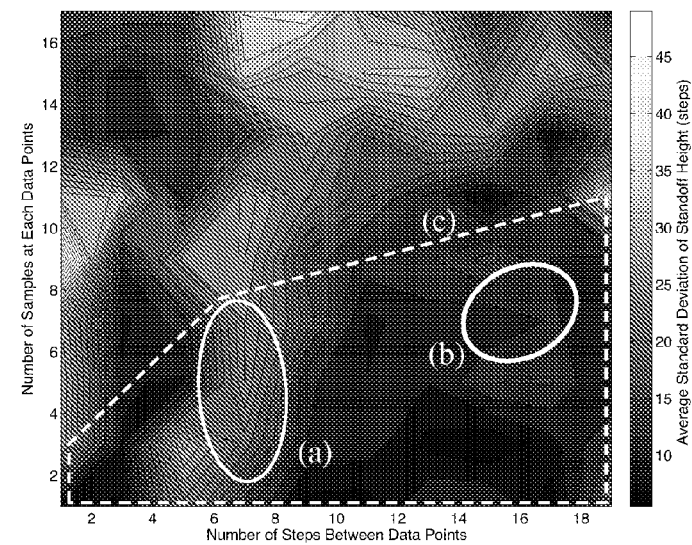

FIG. 7 shows the standard deviations of each of the permutations discussed above. As seen, region (b) has the lowest standard deviation representing the permutation of scan parameters that offers the best combination of speed and accuracy for this given example.

Having discussed an initial signal intensity adjustment algorithm embodiment above, a readjustment algorithm embodiment will now be discussed. A readjustment algorithm can be based on an assumption that the location on the IC being inspected was fairly close to the previous inspection location and required the same general focusing standoff height. With this assumption, the center point of the fine scan can be the previous global maximum instead of the initial global maximum found by the inaccurate initial scan.

Figure 8:
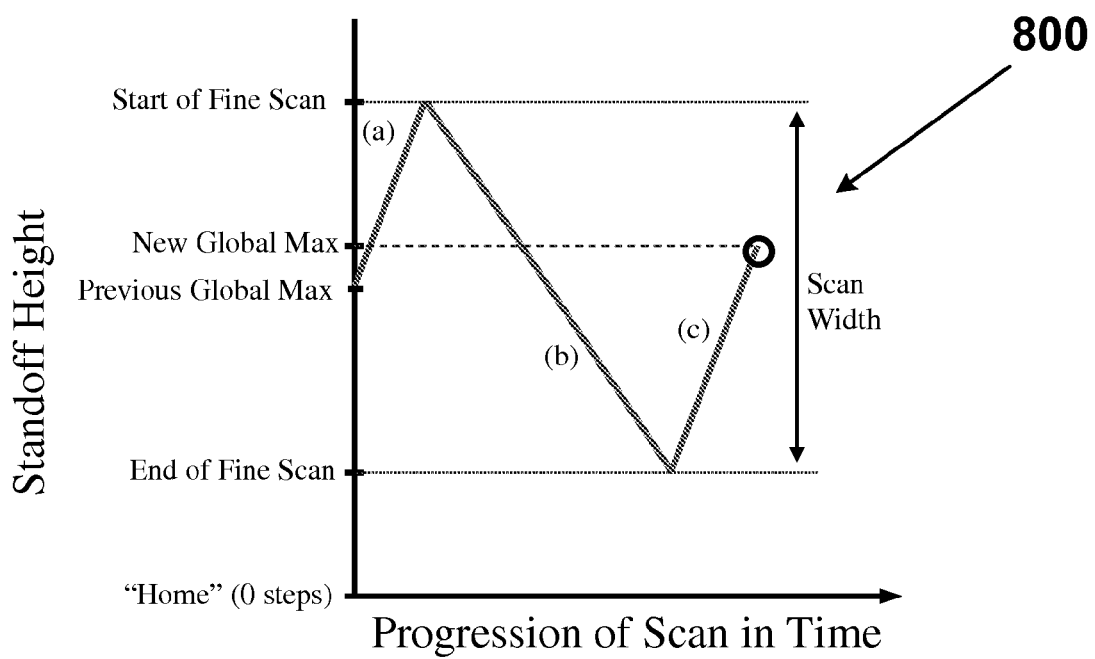
FIG. 8 illustrates a timing diagram showing a readjustment method in accordance with some embodiments of the present invention.

FIG. 8 illustrates a timing diagram 800 showing a readjustment method in accordance with some embodiments of the present invention. The timing diagram 800 illustrates how the focusing head (e.g., the vibrometer head 127) moves as a scan is progressing through the readjustment routine, from the standoff height of the previous global maximum to the standoff height of a new global maximum of the signal intensity profile. The lines in the diagram are not showing the velocity of the focusing head, but represent general focusing head motion during a scan.

FIG. 8 shows a routine that is very similar to the routine shown in FIG. 4, having lines (a), (b), and (c), as detailed below. Line (a) shows the focusing head moving up at full speed to half of the scan width to the starting position of the precise scan. The head then moves down, shown by line (b), at a speed governed by the number of steps between data points (standoff height resolution) and the number of samples of the signal intensity strength averaged at each data point. When the fine scan is finished, the focusing head then moves back up at full speed to the location where the highest amplitude of the signal intensity strength of the vibrometer was found during the fine scan, as shown by line (c). Like the initial scan, the three main parameters controlling accuracy and scan time were standoff height resolution, the number of samples averaged at each data point, and the scan width.

In addition to standoff height, the roughness of the surface being scanned can have an effect on signal intensity. An additional algorithm to take into effect surface roughness can be used and implemented in accordance with embodiments of the present invention. The X-Y positioning stage (e.g., the X-Y stage 110) can have a bidirectional repeatability. A Test was conducted to understand how that variation in inspection location on the chip affects the vibrometer signal intensity. Test results indicate that surface roughness can affect the signal intensity of the vibrometer. If an unsatisfactory signal intensity strength is found at a specific location, a small change in inspection location has the potential of resulting in a stronger signal intensity without altering the accuracy of the IC inspection results.

To implement this X-Y scanning feature in an IC/PCB module scanning embodiment, scanning algorithm embodiments can control both the vibrometer adjustment system and the X-Y positioning stage. First, the item being scanned can be positioned at an initially desired location. The signal intensity strength can be measured by the vibrometer adjustment system and if the signal strength was above a preset threshold, the system would not adjust and immediately instruct the operator to capture data. If the signal strength was below the threshold, the system would readjust to find the standoff height that correlated with a stronger signal intensity. If the signal strength was above the threshold, the script would instruct the operator to capture data. If the signal strength was still below the threshold, the script would start moving the chip to attempt to locate an alternate inspection location that would produce a stronger signal.

In some embodiments, a spiral search pattern can be employed. For example, a spiral search pattern can start at an original location and spiraling out in a 1 micro-meter grid. The grid can have ±3 micro-meter corresponding to half the repeatability of the position stage, producing 48 alternate test locations. As the scan moves from location to location, signal strength is measured. If the signal strength is above the threshold, the search would stop and a data capture occurs. If the signal strength remains below the threshold, the item being scanned moves to the next location in the spiral grid. In some embodiments, the system can readjust to attempt to maintain the proper standoff height while minimizing searching time. For example, such readjustment can be carried our every 4th scan. If on completion of the scanning pattern a value above the threshold was not found, the stage would move the chip back to the location where the strongest signal was found, readjust, and capture data.

FIG. 9 (collectively FIGS. 9A & 9B) illustrates sample correlation plot diagrams showing comparisons of good and bad chips versus reference data to show how embodiments of the present invention can assist in differentiating between good and defective devices and/or solder bumps within devices. These figures illustrate a sampling of data to show how embodiments of the present invention can aid in differentiating between good and bad devices. In accordance with one embodiment, an inspection system can take data readings at predetermined locations along the periphery of a device (e.g., an IC). These data readings can be compared to reference data from an IC known to be a good device. Resulting comparison data can be used to create plot diagrams, such as FIGS. 9A and 9B to aid in distinguishing good ICs from bad ICs. It should be understood that the plots in FIG. 9 are exemplary only and that other plots can be produced to help differentiate between devices.

Figure 10:
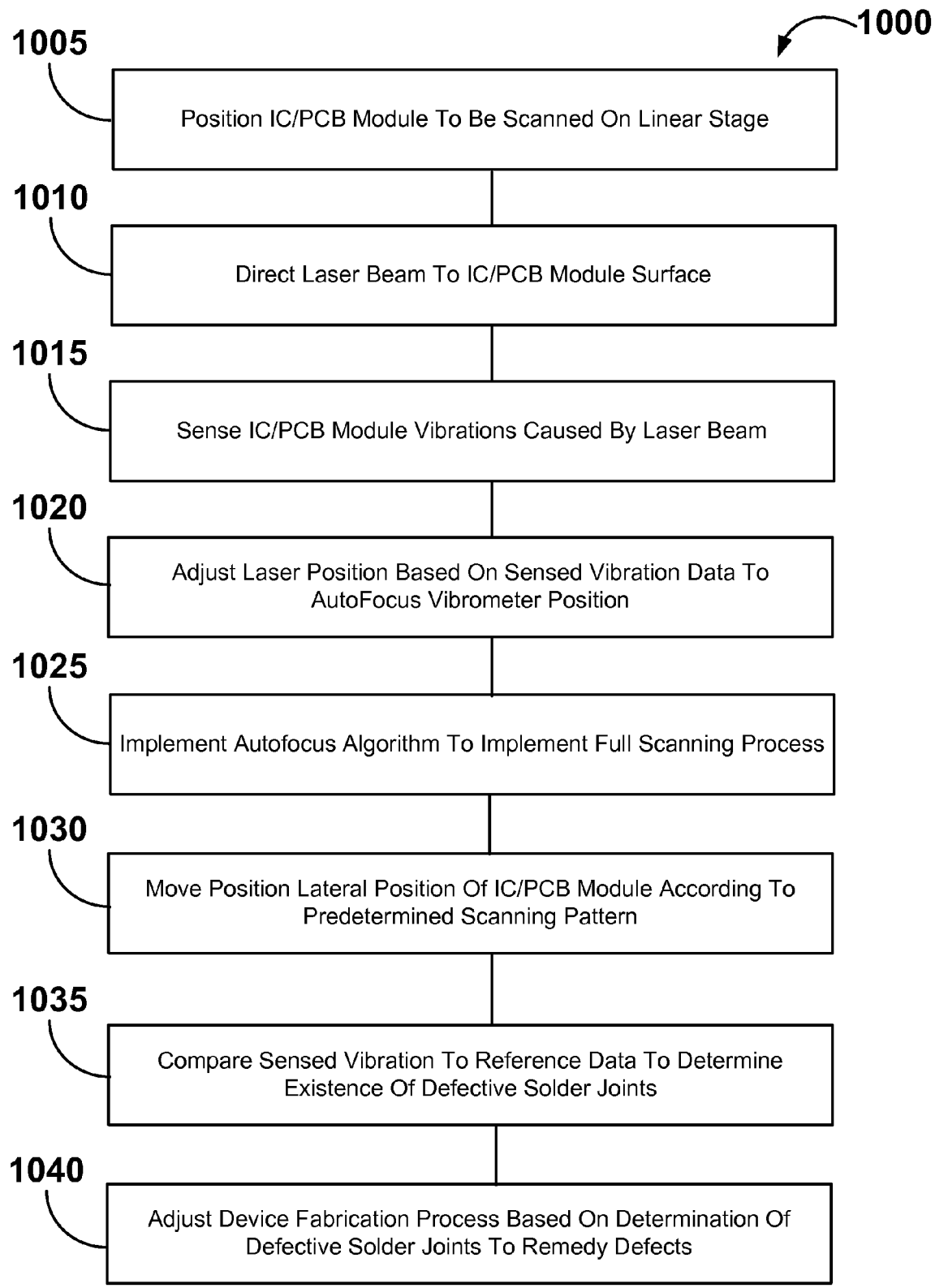
FIG. 10 illustrates an IC/solder joint testing method in accordance with some embodiments of the present invention.

As mentioned above, embodiments of the present invention can also include method or process embodiments. FIG. 10 illustrates an IC/solder bump testing method 1000 in accordance with some embodiments of the present invention. Those skilled in the art will understand that method 1000 can be performed in various orders (including differently than illustrated in FIG. 10), additional actions can be implemented as part of a method embodiment, and that some actions pictured in FIG. 10 or discussed below are not necessary. In addition, it should be understood that while certain actions illustrated in FIG. 10 may be discussed herein as including certain other actions, these certain other actions may be carried out in various orders and/or as parts of the other actions depicted in FIG. 10. Method embodiments of the present invention, such as the one depicted in FIG. 10, may be implemented with the devices and systems discussed herein. Method embodiments may also be coded in a programming language, stored in a memory, and implemented with a processor or microcontroller. Method embodiments can also include the use of component devices and a processor can be used to manage operation of component devices as desired.

The method 1000 can initiate with an object to be scanned being positioned at an appropriate scanning location at 1005. The object to be scanned can be, for example, an IC package, PCB, silicon die (chip), silicon wafer, chip capacitor or IC/PCB module containing solder bumps. The scanning location can be a linear stage (e.g., the X-Y linear stage 110). The method 1000 can continue by directing energy toward a device and then sensing data from the device. For example, at 1010 the method can include directing laser beam (e.g., a pulsed laser) at an IC/PCB module and, at 1015 sensing IC/PCB module vibrations caused by the laser beam. In some embodiments, a YAG laser module can be used to provide the laser beam energy and the laser/vibrometer can be used to sense and read vibrational data.

According to some method embodiments of the present invention, the scanning environment can be altered to obtain optimal scanning data. For example, the laser/vibrometer module position can be modified at 1020 to autofocus the vibrometer. Movements can be accomplished by changing the offset distance between the laser/vibrometer module and the scanned object. Movements such as this can aid in obtaining better scanning data for use in detecting non-optimal solder bumps.

Movements can be carried in both lateral and vertical positions. For example, at 1025, an autofocus algorithm can be followed to vertically modify the scanning environment. Vertical movement can used to fine a position having the highest signal intensity strength for a particular type of scanned object. Control of vertical movement can be made in response to scanned data that is used as a feedback control data. In addition, at 1030, movement can be done laterally (X-Y plane). Lateral movement can be done in accordance with a predetermined scanning pattern. In some scanning arrangements, it may be advantageous to employ lateral movement due to undesired roughness surface of an object being scanned.

Employing the method 1000 can also lead to determining whether defects exist in one or more solder bumps. For example, at 1035, data can be captured during a scanned and compared with reference data to determine existence of defective solder bumps. The reference data can be stored in a memory for comparison purposes. The reference data can be a predetermined threshold or a signature scanning pattern from a known non-defective object, such as a known IC/PCB module with non-defective solder bumps.

Based on the outcome of the comparison, the method 1000 can also include adjusting a fabrication process at 1040. Adjustment of a fabrication process can be done to remedy any discovered defects and can include modifications to resolve errors causing production of faulty devices, such as defective IC/PCB modules with defective solder joints or silicon die.

The embodiments of the present invention are not limited to the particular formulations, process steps, and materials disclosed herein as such formulations, process steps, and materials may vary somewhat. Moreover, the terminology employed herein is used for the purpose of describing exemplary embodiments only and the terminology is not intended to be limiting since the scope of the various embodiments of the present invention will be limited only by the appended claims and equivalents thereof. Indeed, the above descriptions are exemplary and yet other features and embodiments exist.

For example, embodiments of the present invention comprise systems and methods to find a strong signal intensity strength of a vibrometer in an automated manner for inspection of IC chips for solder bump defects. By removing the need to manually adjust the laser vibrometer, human variation was removed from the inspection prototype, increasing the repeatability of the defect detection. Shorter adjustment and scan times can be achieved by using an automated vibrometer adjustment system as discussed herein. Enabling fast data capture to occur will increase throughput and quality while reducing the cost of the products being inspected. This benefits device producers and end consumers.

Therefore, while embodiments of the invention are described with reference to exemplary embodiments, those skilled in the art will understand that variations and modifications can be effected within the scope of the invention as defined in the appended claims. Accordingly, the scope of the various embodiments of the present invention should not be limited to the above discussed embodiments, and should only be defined by the following claims and all equivalents.

We claim:

1. A non-destructive solder joint inspection system for testing a plurality of solder joints disposed within a device, the system comprising:
   a laser module for producing a pulsed laser beam used to excite a device containing a plurality of solder joints to vibrate the device;
   an interferometer module disposed to sense vibration displacements created in the device by the pulsed laser beam;
   a system controller to receive vibration data from the interferometer, the system controller configured to output a control signal for adjusting a position of the laser module relative to the device in a horizontal plane and a vertical plane; and
   the system controller further configured to adjust the device in a spiral search pattern.

2. The system of claim 1, wherein the system controller is configured to determine if the plurality of solder joints are reliable bonds by comparing received vibration data to reference data.

3. The system of claim 2, wherein the reference data comprises at least one of a threshold reference and a vibration signature of at least one non-defective device.

4. The system of claim 1, wherein the system controller is further configured to adjust the relative distance between the laser module and the device so that the interferometer module is positioned at a maximum focusing location relative to the device.

5. The system of claim 1, wherein the laser module and the interferometer module are separate stand-alone components.

6. The system of claim 1, wherein the system controller is configured to autofocus the interferometer module responsive to the received vibration data.

7. The system of claim 1, wherein the system controller is configured to autofocus the interferometer unit responsive to the received vibration data via an initial scan of the device and a second scan of the device, wherein the initial scan and the second scan include receiving varied vibration data.

8. The system of claim 1, the system controller comprising a memory that stores an executable program that, when executed by a processor of the system controller, enables the system controller to adjust a relative distance between the laser module and the device.

9. The system of claim 1, further comprising a linear actuator stage to carry and move at least a portion of the interferometer module responsive to a control signal provided by the system controller.

10. The system of claim 1, wherein the interferometer is adapted to sense signal intensity of reflected laser energy from the device to provide same to system controller for use in adjusting a relative distance between the laser module and the device.

11. The system of claim 1, further comprising one or more of an operator controller and an operator interface.

12. A method to test solder joints in a device, the method comprising:
   directing a pulsed laser beam to the device comprising a plurality of solder joints so as to make the device vibrate;
   receiving vibration data from the device with an interferometer; and adjusting a position of the intereferometer relative to the device in a vertical plane and horizontal plane in response to the received vibration data to focus the interferometer,
wherein the adjusting comprises moving the device in a spiral search pattern.

13. The method of claim 12, further comprising comparing the received vibration data to reference data to determine whether the solder joints are reliable.

14. The method of claim 12, further comprising comparing the received vibration data to vibration data of a non-defective device to determine whether the device being tested is defective.

15. The method of claim 12, wherein adjusting the distance between the intereferometer and the device comprising a multi-stage focus process, with the first stage being optimized for speed and the second stage being optimized for accuracy.

16. The method of claim 12, further comprising comparing the received vibration data to reference vibration data of a non-defective chip to determine a type of defect in the device.

17. The method of claim 12, further comprising adjusting one or more process steps of a fabrication process so that a subsequent device is non-defective.

18. The method of claim 12, wherein adjusting the distance between the interferometer and the device is done to provide a stand off distance between the interferometer and the device so that the interferometer senses a strong intensity strength.

19. The method of claim 12, wherein adjusting the distance between the interferometer and the device comprises a multi-stage focus process, the first stage being an initial auto-focusing stage and a subsequent refocusing stage.

20. The method of claim 12, further comprising providing the interferometer and the laser as separate stand-alone modules positioned toward the device.

21. The method of claim 12, further comprising a linear stage to carry and move the laser and the interferometer relative to the device.

22. An apparatus to detect defective solder joints, the apparatus comprising:
a laser vibrometer disposed in a position to scan a device by sensing vibrational data from the device, the device comprising a plurality of solder joints;
a system controller in electrical communication with the laser vibrometer and configured to receive the vibrational data, the system controller further configured to process the vibrational data to determine whether any one of the solder joints is defective;
wherein the system controller is further configured to adjust a position of the laser vibrometer relative to the device in a vertical plane and a horizontal plane enabling the laser vibrometer to receive vibrational data at a high intensity level; and
wherein the system controller is further configured to adjust the laser vibrometer in a spiral search pattern.

23. The apparatus of claim 22, further comprising a laser module disposed in a position and configured to direct a pulsed laser beam toward the device such that the device becomes excited and vibrates.

24. The apparatus of claim 22, wherein the system controller is configured to autofocus the vibrometer based in response to processed vibrational data.

25. The apparatus of claim 22, wherein the vibrational data is in the form of reflected optical energy being reflected from the device.

26. The apparatus of claim 22, wherein the system controller is configured to control the vibrometer to sense vibrational data at a plurality of unique locations on the device to obtain a vibration signature for the device.

27. The apparatus of claim 26, wherein the system controller compares the vibration signature of the device to a reference vibration signature to determine whether the device has reliable solder joints.

28. The apparatus of claim 22, further comprising a linear stage to carry the vibrometer and configured to vertically adjust the vibrometer and an X-Y stage to hold the device and configured to move the device in a horizontal plane and adjust the device relative to the vibrometer to improve the signal intensity value.

29. The apparatus of claim 22, wherein the system controller is configured to test a plurality of different devices and obtain vibrational data from the plurality of devices by auto-focusing the vibrometer to sense vibrational data from each of the plurality of devices.

30. A method to test for the reliability of solder joints disposed in a device, the method comprising:
positioning the device to be excited so that the device enters a mechanical vibration state in which the device vibrates;
sensing mechanical vibration data from the device at a plurality of locations on the device with an interferometer by auto-focusing a relative position of the interferometer relative to the device in a horizontal and vertical plane, and based on the vibration data, determining if solder joints within the device are reliable; and
adjusting the device in a spiral search pattern.

31. The method of claim 30, further comprising exciting the device with a pulsed laser and sensing mechanical vibration data by receiving reflected light from the device.

32. The method of claim 30, further comprising adjusting a relative distance between the interferometer and the device with a multi-phase focusing algorithm so as to autofocus the interferometer to sense mechanical vibration data.

33. The method of claim 30, wherein sensing mechanical vibration data from the device comprises obtaining a vibration signature for the device and determining if solder joints within the device are reliable comprises comparing the vibration signature to reference data.

34. The method of claim 30, wherein the device is a printed circuit board that comprises a plurality of IC chips disposed on the board.

35. The method of claim 30, further comprising determining focusing algorithm parameters to determine optimal auto focusing parameters for the device being focused on.

36. The method of claim 35, wherein determining the focusing algorithm parameters is automated by the system to determine the optimal auto focusing parameters for the device being focused on.

37. An autofocus system for an interferometer to maintain a strong signal intensity level, the system comprising:
an interferometer module disposed to receive reflected laser energy from the device to sense vibration displacements in the device;
a system controller to receive signal intensity data from the interferometer, the system controller configured to output a control signal for adjusting a relative distance and position between the interferometer and the device in a horizontal plane and a vertical plane through a focusing algorithm; and
the system controller further configured to adjust the device in a spiral search pattern.

38. The system of claim 37, wherein the system controller is further configured to adjust the relative distance between a laser module and the device so that the interferometer module is positioned at a maximum focusing location relative to the device to achieve to strongest signal intensity possible.

39. The system of claim 37, wherein the system controller is configured to autofocus the interferometer unit responsive to the received vibrometer signal intensity data.

40. The system of claim 37, wherein the system controller is configured to autofocus the interferometer unit responsive to the received vibrometer signal intensity data via an initial scan of the device and a second scan of the device, wherein the initial scan and the second scan include receiving varied vibrometer signal intensity data.

41. The method of claim 37, wherein adjusting the distance between the vibrometer and the device comprising a multi-stage focus process, with the first stage being optimized for speed and the second stage being optimized for accuracy.

42. The system of claim 37, the system controller comprising a memory that stores an executable program that, when executed by a processor, enables the system controller to adjust a relative distance and position between the laser module and the device.

43. The system of claim 37, further comprising a linear actuator stage to carry and move at least a portion of the interferometer module responsive to a control signal provided by the system controller.

44. The system of claim 37, further comprising an X-Y stage to carry and move the device relative to the interferometer to find a location on the device for recording vibration data through the interferometer.

\* \* \* \* \*